United States Patent [19]
Löken

[11] 3,935,194
[45] Jan. 27, 1976

[54] SEPARATION OF HECOGENIN-TIGOGENIN MIXTURES

[75] Inventor: Bjarte Löken, Milan, Italy

[73] Assignee: Omni Research Incorporated, San German, P.R.

[22] Filed: Jan. 22, 1974

[21] Appl. No.: 435,465

[52] U.S. Cl. .................................. 260/239.55 A
[51] Int. Cl.² .................................. C07J 17/00
[58] Field of Search ....................... 260/239.55 A

[56] References Cited
UNITED STATES PATENTS

| | | | |
|---|---|---|---|
| 2,991,282 | 7/1961 | Rubin | 260/239.55 A |
| 3,172,884 | 3/1965 | Lewin et al. | 260/239.55 A |
| 3,303,187 | 2/1967 | Rubin | 260/239.55 A |

Primary Examiner—Elbert L. Roberts
Attorney, Agent, or Firm—Fidelman, Wolffe & Leitner

[57] ABSTRACT

A process for separating hecogenin-tigogenin mixtures which involves acetylating the mixed genins, then solvent recrystallization separation of the mixed genin acetates, crystallizing out hecogenin acetate from a non-polar solvent, tigogenin acetate from a polar solvent. A sequential sequence is contemplated to first recover the predominant genin, then the less-predominant genin.

Preferred source materials are crude 5–25% sapogenin content acid hydrolyzates of Agave leaf juice. Specifically preferred is the acid hydrolyzate from fresh Agave leaf juice obtained prior to decortication.

5 Claims, No Drawings

SEPARATION OF HECOGENIN-TIGOGENIN MIXTURES

This invention relates to separating crude mixed hecogenin-tigogenin into the constituent genins. In a preferred embodiment, this invention relates specifically to the recovery of pure hecogenin and/or tigogenin from a crude genin product obtained by hydrolysis of concentrated in saponin agave leaf juices.

As is well known, the leaf juices of sisal, henequen, cabuya and the like (*Agave sisalana, A. furcroides, A. lentonaceum, A. Mexicana*) contain saponins in a dilute solution therein. The saponins are convertable to (the water insoluble) sapogenins by hydrolysis reactions. Since agave plants are widely cultivated for the fiber content of their leaf, workers in the steroid arts have explored the concept of securing sapogenins as a fiber by-product, having met with some success. For further discussion of sisal leaf juices as a steroid source material and for a preferred procedure to obtain a crude sapogenin product which looks like coffee grounds reference is made to co-pending application Ser. No. 435464 now U.S. Pat. No. 3,895,999, filed concurrently herewith. The "coffee grounds" form a preferred source material for practice of this invention.

Hecogenin-tigogenin mixtures also result from what is known as a total juice treatment of certain agave leaves and, indeed, may occur within other contexts. Accordingly, the practice of the present invention is applicable to separation of hecogenin-tigogenin mixtures, however such mixture is derived. Even so, the detailed practice of this invention may be best appreciated by further explanation thereof within the rationale of an agave leaf source for the hecogenin-tigogenin mixture.

Many species of agave are cultivated for their fiber content. Recoverable quantities of one sapogenin or another, sometimes in admixture, are available in saponin form in the leaf juices of commonly cultivated agave species. In particular, a hecogenin-tigogenin mixture will result from acid hydrolysis of many, but not all, agave plants leaf juice. An exception is *Agave sisalana* which, in Africa, gives rise to a sapogenin product consisting almost exclusively of hecogenin. However, the same species, when grown in Haiti, produces a hecogenin-tigogenin mixture with from 14–35% tigogenin. From the Mexican henequen (*Agave furcroides*), a mixed product is obtained with 60–75% hecogenin, balance mostly tigogenin. The cabuya in Colombia produces a mixture of four sapogenins, including hecogenin and tigogenin. Sources of tigogenin include the local henequen in Honduras, essentially *Agave lentonaceum* and, in a mixture with hecogenin, the henequen from the state of Tamaulipas in Mexico. Both hecogenin and tigogenin have commercial potential as sources for medically useful steroids. However, absent an effective, commercially feasible technique for separation of hecogenin-tigogenin mixtures, efforts to obtain individual sapogenins from Agave leaf sources must be seriously hampered. Some of the most promising sites for steriod recovery purposes, as for example the highly efficient sisal plantations in Mexico, may well be ruled out because treatment of the juices from the sisal leaf grown there produces a hecogenin-tigogenin mixture.

The object of the present invention is to provide an efficient procedure for separating hecogenin-tigogenin mixtures.

A further object of the present invention is to provide an efficient procedure for separating hecogenin and tigogenin from the mixed genin product resulting from hydrolysis of agave leaf juices.

Hecogenin (3β-hydroxy-5α,22α-spirostan-12-one) differs from tigogenin (3β-hydroxy-5α,22α-spirostane) only by the presence of the 12 keto group, as can be seen in the following formula:

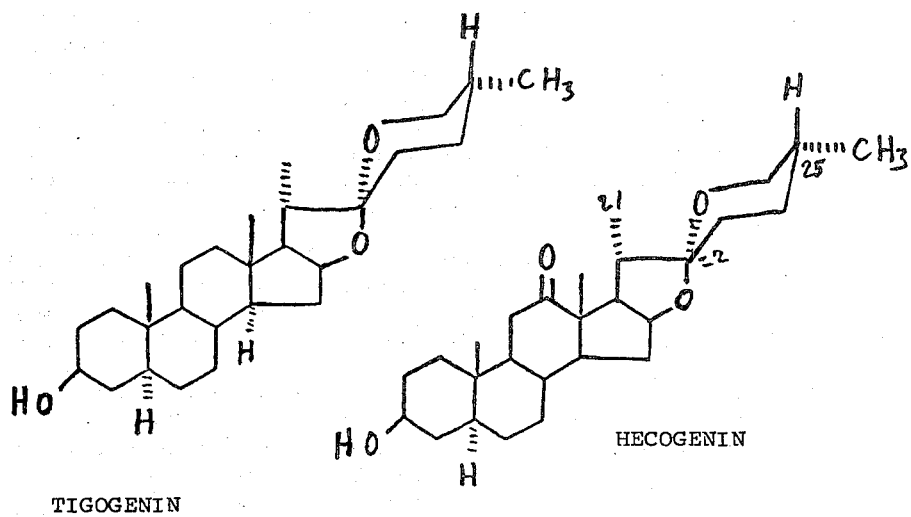

TIGOGENIN                HECOGENIN

Separation of hecogenin-tigogenin mixtures is made difficult by the exceedingly close relationship of the two compounds. Basically, they are soluble or insoluble in the same solvents. If one genin is predominant, some crystallization separation can be effected. Nonetheless, a substantial loss results if the mother liquor mixture of the two genins cannot be separated. However, when the 3-hydroxy group is acetylated, the differences in solubility of the acetates in polar (e.g. alkanol, ketones, etc.) and non-polar solvents (e.g. alkyl, cycloalkyl hydrocarbons) is enhanced likely because the 12 keto group of hecogenin will then contribute a large incremental precentage to the polarity and, of consequence, to solubility in polar solvents, to less solubility in non-polar solvents. Preferred polar solvents for the separation are methanol, ethanol, isopropanol, acetone, methyl ethyl ketone. Preferred non-polar solvents for the separation are hexane, heptane, cyclohexane, methylcyclohexane.

Accordingly, practice of the present invention contemplates conversion of a hecogenin-tigogenin mixture into the mixed acetates thereof and crystallization recovery from an appropriate solvent. Thus for isolation of an acceptable tigogenin product from Agave lentonaceum, the mixed acetates are crystallized from a polar solvent (such an methanol), which crystallization results in a crystalline, relatively pure tigogenin acetate product leaving the hecogenin acetate behind in the solution in the concentrated mother liquor.

In the instance where the original source material of the mixed genin is *Agave sisalana* and *Agave furcroides*, wherein the sapogenin is a mixture containing from about 60–85% hecogenin, balance tigogenin, the mixed genin acetates may be recrystallized from heptane, in which solvent the tigogenin acetate is the more soluble constituent and remains in solution in the mother liquor.

The separation can be conducted sequentially, wherein first the one component is recovered (for example, relatively pure crystalline hecogenin acetate from heptane solution), then the mother liquor is evaporated to dryness. Afterward, the dried residue is redissolved in the counterpart solvent and the component is recovered (for example, relatively pure tigogenin acetate from methanol solution).

In any event, the now separated genin acetate can be hydrolyzed to provide the relatively pure genin, i.e. hecogenin and/or tigogenin.

The above description of the process of this invention has been posed within the context of separating already purified hecogenin-tigogenin mixtures. However, when Agave leaf constitutes the original source of the genin mixture, a relatively crude material may constitute the available source material. That is because sapogenin recovery at any one decorticator site will frequently involve limited treatment facilities and daily recovery of relatively small quantities of sapogenins in the form, for example, of an acid hydrolyzate containing 5–25% sapogenins, i.e. the water insoluble product material obtained by acid hydrolyzing Agave leaf juice saponins and hemisaponins.

A central purification and genin separation facility can readily handle the crude sapogenin produced from several Agave leaf (e.g. sisal) decorticator sites. Accordingly, practice of this invention includes also a preliminary solvent extraction purification of the hecogenin-tigogenin mixture being separated.

The crude sapogenin mixture obtained from treatment of Agave leaf juices remaining after decortication of the fiber contain substantial interfering impurities. Mixtures obtained from work-up of the secondary juices expressed from the residual leaf pulp will often contain even more interfering impurities. Such crude sapogenin mixtures require selective solvents such as the straight chain paraffin solvents to recover the hecogenin and tigogenin content from the crude mixture. However, when the crude mixture is obtained from virgin juice according to practice of the invention described in copending application Ser. No. 435,464 now U.S. Pat. No. 3,895,999, filed concurrently herewith, only traces of contaminating lipoids and other interfering plant material is present. This "coffee grounds" product is a preferred source material for practice of this invention. Briefly stated, the "coffee grounds" constitute the acid hydrolyzate product from fresh leaf juice obtained prior to decortication of the leaves.

In general the acid hydrolyzate (5–25% sapogenins) can be purified by extraction with hydrocarbon solvents. The straight chain paraffins have relatively low solubility for hecogenin, but are more selective. The aromatics, like toluene, benzene, xylene, and the isocyclics, have greater solubility properties so less solvent is needed, but these solvents are less selective. When the "coffee grounds" acid hydrolzate from virgin juice constitutes the starting material, only traces of lipoid are present. Toluene is the preferred solvent. Usually the sapogenin extract recovered from the toluene does not require recrystallization; may be employed directly in the hecogenin-tigogenin separation procedure.

For further understanding of the invention, the following specific examples thereof are presented:

EXAMPLE I

At a Mexican sisal estate decorticator, virgin sisal juice was obtained by squeezing feshly cut leaves at the rate of 30,000 leaves per hour (300,000 leaves per 10 hour working day) past smooth rollers set so that 15,000 liters of clear virgin juice was obtained over the 10 hour day, expressing about 10% of the leaf weight as juice. The freshly expressed juice was screened to remove plant debris and any other solid matter.

The clear juice was pumped into a 1500 gal. jacketed open reactor-evaporator tank (6,000 liters). The tank was heated by low pressure steam to boil away juice at a rate lower than the juice feed rate. When the 1500 gal. tank was about full, the flow of virgin juice was diverted to a 1,000 gal. purge tank, which also was an open jacketed steam heated vessel. As soon as the evaporator-reactor tank was filled with juice, 54 kg. techn. conc. sulfuric acid diluted to 100 l with ice water, was added. The boiling was continued so as to hydrolyze simultaneously with further evaporation. The incoming juice diverted to the purge tank was kept boiling and, at intervals, the juice level in the 1,500 gal. (hydrolysis) reactor-evaporator tank was made up by pumping in hot, partially evaporated juice from the purge tank. An exact record was kept on the total amount of juice handled through flow meter control. (The combined evaporation/hydrolysis reactor could be run with relatively high steam pressure heating because no foaming occurred.)

About one hour after shutting down the rollers and the decorticator for the night, the whole 15,000 l of fresh juice had been added to the evaporator-reactor tank and the purge tank was empty. At this point, the pH was found to be 0.9 and 25kg more sulfuric acid (conc. tech.) was added, which brought the pH to 0.5. Four more hours of boiling was sufficient to complete hydrolysis. The reaction product slurry was filtered immediately after cooling (by passing water through the jacket), so as to complete the processing sequence before start of the morning shift. Obtained was 160 kg of "coffee grounds"; 7% sapogenin content.

The "coffee grounds" product was exhaustively extracted with toluene, followed by evaporation of the toluene extract to concentrate the mother liquor, and crystallize out the mixed genins.

2.5g of the first crop of sapogenin mixture, obtained from the processing, which by thin layer chromatography showed a ratio of hecogenin to tigogenin of 7:3, was heated in 5ml pyridine and 3.5ml acetic anhydride at 100°C. for 1.5 hours. A few drops of water was then added and the temperature maintained for 20 minutes more to react away the excess anhydride. 4ml water was added, and the mixture left standing at room temperature. The crystals were filtered, washed with water, methanol and hexane in succession, collected and dried. 2.7g genin acetate was obtained with about the same H/T ratio as the starting 3-hydroxy mixture (by TLC).

This material was recrystallized by dissolving in 300ml of heptane at reflux temperature. The clear solution was concentrated to 65ml, cooled to ambient temperature, and the crystallization product filtered. Washing with a little heptane, collection and drying gave 1.9g of material in well developed prismatic crystals of slightly green color (chlorophyll), and which on TLC (80% benzene, 20% ethyl acetate) analyzed as essentially hecogenin acetate with only a shade of the tigogenin acetate (corresponding to 0.95H and 0.05% approximately). M.p: 243°–244°C., Saponification gave hecogenin m.p. 262°–263°.

EXAMPLE II

The heptane filtrate mother liquor from Example I above was concentrated to dryness under reduced pressure. The residue in the flask was refluxed with 25ml methanol, and allowed to cool slowly to room temperature. 400mg of crystals was obtained which, on TLC, was assayed as 93% tigogenin acetate m.p. 199°.

EXAMPLE III 2.5g sapogenin obtained from *Agave lentonaceum* from the Republic of Honduras was found to be about 80% tigogenin by TLC. The remainder was hecogenin and 9(11)-dehydrohecogenin. This material was acetylated as described in Example I. The crude acetate was dissolved by refluxing with liberal quantities of methanol. The clear solution was evaporated to a final volume of 70ml and allowed to cool slowly to ambient temperature. The resulting crystals were filtered, washed with a little methanol, collected and dried. 1.8g of tigogenin acetate was obtained, m.p. 202°–206°, $(\alpha)_D$, $-75°$(Chlf). TLC showed this material to be better than 95% pure.

What is claimed is:

1. A method for separating a hecogenin-tigogenin mixture predominant in hecogenin which comprises acetylating the mixed genins, then dissolving the resulting mixed acetates in a non-polar solvent, and thereafter crystallizing out a relatively pure hecogenin acetate, the tigogenin acetate remaining in solution in the mother liquor.

2. A method for separating a hecogenin-tigogenin mixture predominant in tigogenin which comprises acetylating the mixed genins, then dissolving the resulting mixed acetates in a polar solvent, and thereafter crystallizing out relatively pure tigogenin acetate, the hecogenin acetate remaining in solution in the mother liquor.

3. A method for separating a hecogenin-tigogenin mixture which comprises:
   acetylating the mixed genins;
   dissolving the resulting mixed acetates in a solvent selected from the group consisting of polar and non-polar solvents, the selection being made according to which genin predominates in the mixture, a polar solvent when tigogenin predominates, a non-polar solvent when hecogenin predominates;
   crystallizing out the predominant acetate in relatively pure crystalline form, the non-predominant acetate remaining in solution in the mother liquor; and
   optionally thereafter evaporating away the mother liquor, redissolving the residue in the previously unselected solvent and crystallizing out therefrom the non-predominant acetate in relatively pure crystalline form.

4. The process of claim 3 wherein a crude sapogenin containing material derived from agave leaf juice constitutes the source material, and wherein said source material is solvent extracted to provide an extract product which constitutes the mixed hecogenin-tigogenin separated by the process of claim 3.

5. The process of claim 5 wherein the solvent employed to extract the crude sapogenin containing material is toluene.

* * * * *